(12) United States Patent
Ambrosen et al.

(10) Patent No.: US 8,697,621 B2
(45) Date of Patent: Apr. 15, 2014

(54) SURFACTANT PRODUCT COMPRISING TWO DISTINCT EFFERVESCENT COMPOSITIONS

(75) Inventors: Helen Elizabeth Ambrosen, Wimborne (GB); Mark Constantine, Poole (GB); Margaret Joan Constantine, Great (GB); Noriko Miura, Great (GB); Jack Contantine, Great (GB)

(73) Assignee: Cosmetic Warriors Ltd., Poole, Dorset (GB)

( * ) Notice: Subject to any disclaimer, the term of this patent is extended or adjusted under 35 U.S.C. 154(b) by 0 days.

(21) Appl. No.: 13/702,511

(22) PCT Filed: Jun. 6, 2011

(86) PCT No.: PCT/GB2011/051061
§ 371 (c)(1),
(2), (4) Date: Jun. 10, 2013

(87) PCT Pub. No.: WO2011/154727
PCT Pub. Date: Dec. 15, 2011

(65) Prior Publication Data
US 2013/0281342 A1    Oct. 24, 2013

(30) Foreign Application Priority Data

Jun. 7, 2010 (GB) .................................. 1009453.0

(51) Int. Cl.
*C11D 3/10* (2006.01)
*C11D 7/26* (2006.01)
*C11D 7/60* (2006.01)

(52) U.S. Cl.
USPC ........... 510/146; 510/117; 510/130; 510/135; 510/141; 510/438; 510/446; 510/477; 510/509

(58) Field of Classification Search
USPC ......... 510/117, 130, 135, 141, 146, 438, 446, 510/477, 509
See application file for complete search history.

(56) References Cited

U.S. PATENT DOCUMENTS

| | | | | |
|---|---|---|---|---|
| 3,962,107 | A | * | 6/1976 | Levin et al. ................... 510/117 |
| 5,578,562 | A | | 11/1996 | Lockhart |
| 6,284,271 | B1 | * | 9/2001 | Lundberg et al. ............. 424/466 |
| 2005/0113279 | A1 | * | 5/2005 | Desmarescaux et al. ..... 510/447 |
| 2006/0078509 | A1 | * | 4/2006 | Gebreselassie et al. ........ 424/48 |

FOREIGN PATENT DOCUMENTS

| | | |
|---|---|---|
| EP | 1 191 092 | 3/2002 |
| GB | 1 492 688 | 11/1977 |
| GB | 2 382 350 | 5/2003 |
| JP | 2 142722 | 5/1990 |
| JP | 3 074321 | 3/1991 |
| WO | WO 00/47181 | 8/2000 |
| WO | WO 01/28513 | 4/2001 |
| WO | WO 2008/072104 | 6/2008 |

OTHER PUBLICATIONS

International Search Report and Written Opinion for International Application No. PCT/GB2011/051061 mailed Apr. 26, 2012.
International Preliminary Report on Patentability as well as Written Opinion for International Application No. PCT/GB2011/051061 issued Dec. 10, 2012.

* cited by examiner

*Primary Examiner* — Charles Boyer
(74) *Attorney, Agent, or Firm* — Merchant & Gould P.C.

(57) ABSTRACT

A surfactant product includes a first effervescent material and a second effervescent material. Each effervescent material is capable of effervescence on contact with water, wherein the rate of effervescence of the first effervescent material is greater than the rate of effervescence of the second effervescent material. The first and second effervescent materials are distinct from each other and at least one of the effervescent materials envelops the other of the effervescent materials.

14 Claims, No Drawings

SURFACTANT PRODUCT COMPRISING TWO DISTINCT EFFERVESCENT COMPOSITIONS

This application is a National Stage Application of PCT/GB2011/051061, filed 6 Jun. 2011, which claims benefit of Serial No. 1009453.0, filed 7 Jun. 2010 in Great Britain and which applications are incorporated herein by reference. To the extent appropriate, a claim of priority is made to each of the above disclosed applications.

FIELD OF THE INVENTION

The present invention relates to a surfactant product, a process for producing said surfactant product, and a product prepared by the method.

BACKGROUND TO THE INVENTION

The present invention relates to surfactants particularly those for use in contact with the human or animal body.

A bath product which has been increasingly popular is the Bath Bomb® or Ballistic®. This products are primarily designed to provide an experience for the user. They contain sodium bicarbonate and citric acid such that on contact with water they effervesce carbon dioxide. This effervescence provides a pleasant sensation for the user. The products also typically contain oils and/or fragrances which are liberated with the effervescence. This liberation adds to the sensory experience of the user. Effervescent products have also been used in other application areas. For example, EP1191092 teaches a cleansing product, in particular for cleaning hard surfaces which effervesces in use. To protect the effervescent product from premature activation, the effervescent material is covered with an outer layer which is non-effervescent. This outer layer is formed from a hydrated version of the inner effervescent layer.

Surfactant products such as bubble baths, shampoos, shower gels and toothpastes are extremely well known cosmetic products and personal care products. Bubble bath products are typically provided in the form of liquids. They are sold in containers to the end user and may be dispensed by the end user. However, the required use of packaging is a disadvantage. From an environmental perspective, waste packaging is a significant problem, despite the availability of recycling. For this reason at least, solid materials for creating bath foam have become increasingly popular. These solid surfactant materials may be in the form of a Bubble Bar®. For example WO00/47181 discloses a surfactant product bubble bar which is solid and in the form of a tablet or bar. When required for use, a portion of the solid product may be 'broken off' the bar and used. The products of WO00/47181 are formed from a composition containing cream of tartar, sodium bicarbonate and a surfactant. Although these products address environmental concerns they suffer certain disadvantages. For example, in use the user must apply the required amount of product to the bath water, for example by holding the solid product under running water. In this way, the required foam is produced. Furthermore, some users may find that they do not provide the same 'experience' that a bath ballistic may provide.

The present invention seeks to provide surfactant products which provide a foam bath with an enhanced experience by the user.

SUMMARY OF THE INVENTION

In a first aspect, there is provided a surfactant product comprising a first effervescent material and a second effervescent material, wherein each effervescent material is capable of effervescence on contact with water, wherein the rate of effervescence of the first effervescent material is greater than the rate of effervescence of the second effervescent material, and wherein the first and second effervescent materials are distinct from each other and at least one of the effervescent materials envelops the other of the effervescent materials.

In a second aspect, there is provided a process for the production of a surfactant product comprising a first effervescent material and a second effervescent material, wherein each effervescent material is capable of effervescence on contact with water, wherein the rate of effervescence of the first effervescent material is greater than the rate of effervescence of the second effervescent material, and wherein the first and second effervescent materials are distinct from each other and at least one of the effervescent materials envelops the other of the effervescent materials,
the process comprising the steps of:
i) preparing the first or second effervescent material;
ii) enveloping the first or second effervescent material with the other of the first or second effervescent material.

In a third aspect, there is provided a product obtained or obtainable by a process for the production of a surfactant product comprising a first effervescent material and a second effervescent material, wherein each effervescent material is capable of effervescence on contact with water, wherein the rate of effervescence of the first effervescent material is greater than the rate of effervescence of the second effervescent material, and wherein the first and second effervescent materials are distinct from each other and at least one of the effervescent materials envelops the other of the effervescent materials, the process comprising the steps of:
i) preparing the first or second effervescent material;
ii) enveloping the first or second effervescent material with the other of the first or second effervescent material.

For ease of reference, these and further aspects of the present invention are now discussed under appropriate section headings. However, the teachings under each section are not necessarily limited to each particular section.

Advantages

We have found that by providing a surfactant product containing two layers, both of which effervesce on contact with water but at different rates, we are able to provide to the user, for example of bath products, with a foaming product that does not require action by the user to create foam other than adding the material to water. This need not be by addition to running water. For example with the present product, once a bath has been run the product may be added to the water. This may be before or after the user immersed themselves in the bath. The sodium bicarbonate and the citric acid in the product then react with water to generate carbon dioxide. This effervescence within the surfactant product generates foam. Furthermore, by virtue of the different effervescence rates, the product may be found to propel itself within the body of water in which it is placed. This may be found to generate patterns of foam that are pleasant to view and further enhance the experience of the user.

DETAILED DESCRIPTION

Composition

As discussed herein, in one aspect of the present invention, there is provided a surfactant product comprising a first effervescent material and a second effervescent material, wherein each effervescent material is capable of effervescence on contact with water,
wherein the rate of effervescence of the first effervescent material is greater than the rate of effervescence of the second effervescent material,
and wherein the first and second effervescent materials are distinct from each other and at least one of the effervescent materials envelops the other of the effervescent materials.

Surfactant products of the present invention are compositions which can substantially sustain their physical shape when unsupported by external means, e.g. packaging etc. Thus, they are considered to be solid, solid like, in solid form or in solid-like form at room temperature.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

As mentioned above, due to the solid form of the compositions of the present invention, external packaging is not required to maintain the shape of the composition.

As discussed herein the first and second effervescent materials are distinct from each other. It will be understood by one skilled in the art that 'distinct from each other' requires that the two (or more) materials may not be mixed such that a single combined material results. Furthermore, one skilled in the art will understand that the two materials have different compositions. Without this the rate of effervescence of the first effervescent material would not be greater than the rate of effervescence of the second effervescent material, and the materials would not be distinct.

As discussed herein the at least one of the effervescent materials envelops the other of the effervescent materials. It will be understood that either the first effervescent material envelops the second effervescent material, or the second effervescent material envelops the first effervescent material. Preferably at least one of the effervescent materials entirely envelops the other of the effervescent materials. It will be understood that in this aspect either the first effervescent material entirely envelops the second effervescent material, or the second effervescent material entirely envelops the first effervescent material.

It is preferred that the second effervescent material (the slower effervescing material) envelops the first effervescent material (the faster effervescing material), particularly it is preferred that the second effervescent material entirely envelops the first effervescent material. In these aspects it is found that water will gradually dissolve through the outer surfactant containing layer resulting in generation of some foam. When water penetrates to the faster effervescing first effervescent material then effervescence increases. This increased effervescence passes through the passage created by the water dissolution of the outer effervescent containing layer. The effervescence passing through this layer significantly increases foam generation. Furthermore, if the passage is relatively narrow the pressure created by the exit of the effervesced gas (carbon dioxide) may propel the surfactant product in the water in which is immersed. By this means the now foam generating device will move within the body of water 'drawing' patterns of foam as it moves. This is highly desirable.

First Effervescent Material

The first effervescent material may be selected from appropriate material which effervesce on contact with water. In one aspect the first effervescent material comprises at least sodium bicarbonate and citric acid. These materials are present in any suitable amounts to achieve effervescence. One skilled in the art is able to combine these materials to provide the desired rate of effervescence.

In a preferred aspect the first effervescent material comprises sodium bicarbonate in an amount of 40 to 75 wt % based on the first effervescent material. In a preferred aspect the first effervescent material comprises sodium bicarbonate in an amount of 45 to 70 wt % based on the first effervescent material. In a preferred aspect the first effervescent material comprises sodium bicarbonate in an amount of 50 to 70 wt % based on the first effervescent material. In a preferred aspect the first effervescent material comprises sodium bicarbonate in an amount of 55 to 70 wt % based on the first effervescent material. In a preferred aspect the first effervescent material comprises sodium bicarbonate in an amount of 60 to 70 wt % based on the first effervescent material. In a preferred aspect the first effervescent material comprises sodium bicarbonate in an amount of approximately 65 wt % based on the first effervescent material.

In a preferred aspect the first effervescent material comprises citric acid in an amount of 24 to 40 wt % based on the first effervescent material. In a preferred aspect the first effervescent material comprises citric acid in an amount of 26 to 38 wt % based on the first effervescent material. In a preferred aspect the first effervescent material comprises citric acid in an amount of 28 to 36 wt % based on the first effervescent material. In a preferred aspect the first effervescent material comprises citric acid in an amount of 30 to 34 wt % based on the first effervescent material. In a preferred aspect the first effervescent material comprises citric acid in an amount of approximately 32 wt % based on the first effervescent material.

In a preferred aspect the first effervescent material further comprises a fragrance. Preferably the fragrance is present in an amount of 0.5 to 4 wt % based on the first effervescent material. In a preferred aspect the first effervescent material comprises fragrance in an amount of 1 to 4 wt % based on the first effervescent material. In a preferred aspect the first effervescent material comprises fragrance in an amount of 2 to 4 wt % based on the first effervescent material. In a preferred aspect the first effervescent material comprises fragrance in an amount of 2.5 to 3.5 wt % based on the first effervescent material. In a preferred aspect the first effervescent material comprises fragrance in an amount of approximately 3 wt % based on the first effervescent material.

In a preferred aspect the first effervescent material comprises sodium bicarbonate in an amount of 40 to 75 wt % based on the first effervescent material and citric acid in an amount of 24 to 40 wt % based on the first effervescent material.

In one aspect the first effervescent material is substantially free of cream of tartar. By substantially free of cream of tartar it is meant the first effervescent material comprises cream of tartar in an amount of less than 1 wt % based on the first effervescent material, such as in an amount of less than 0.5 wt % based on the first effervescent material, such as in an amount of less than 0.1 wt % based on the first effervescent material, such as in an amount of less than 0.01 wt % based on the first effervescent material, such as in an amount of less than 0.001 wt % based on the first effervescent material, such as in an amount of less than 0.001 wt % based on the first effervescent material. In one aspect the first effervescent material is free of cream of tartar.

In one aspect the first effervescent material is substantially free of surfactant. By substantially free of surfactant it is meant the first effervescent material comprises surfactant in an amount of less than 1 wt % based on the first effervescent material, such as in an amount of less than 0.5 wt % based on the first effervescent material, such as in an amount of less than 0.1 wt % based on the first effervescent material, such as in an amount of less than 0.01 wt % based on the first effervescent material, such as in an amount of less than 0.001 wt % based on the first effervescent material, such as in an amount of less than 0.001 wt % based on the first effervescent material. In one aspect the first effervescent material is free of surfactant.

Second Effervescent Material

The second effervescent material may be selected from appropriate material which effervesce on contact with water. In one aspect the second effervescent material comprises at least a surfactant, sodium bicarbonate, citric acid and cream of tartar. These materials are present in any suitable amounts to achieve effervescence. One skilled in the art is able to combine these materials to provide the desired rate of effervescence.

In a preferred aspect the second effervescent material comprises surfactant in an amount of 0.5 to 5 wt % based on the second effervescent material. In a preferred aspect the second effervescent material comprises surfactant in an amount of 1 to 5 wt % based on the second effervescent material. In a preferred aspect the second effervescent material comprises surfactant in an amount of 1.5 to 4.5 wt % based on the second effervescent material. In a preferred aspect the second effervescent material comprises surfactant in an amount of 2 to 4 wt % based on the second effervescent material. In a preferred aspect the second effervescent material comprises surfactant in an amount of 2.5 to 3.5 wt % based on the second effervescent material. In a preferred aspect the second effervescent material comprises surfactant in an amount of approximately 3 wt % based on the second effervescent material.

The second effervescent material of the surfactant product of the present invention comprises a surfactant. The surfactant is primarily selected from those surfactants known in the art to be suitable for contact with the skin. In one embodiment, the surfactant is selected from the group consisting of sodium laureth sulfate, cocamide diethanolamine, lauryl betaine and mixtures thereof. In one embodiment, the surfactant is sodium laureth sulfate.

The surfactant of the surfactant product provides the composition with the ability to achieve its required purpose. Thus for a bubble bath, the surfactant creates foam and removes dirt and grease from the user's skin. In one embodiment, the surfactant product is a bubble bath.

In a preferred aspect the second effervescent material comprises sodium bicarbonate in an amount of 40 to 75 wt % based on the second effervescent material. In a preferred aspect the second effervescent material comprises sodium bicarbonate in an amount of 45 to 70 wt % based on the second effervescent material. In a preferred aspect the second effervescent material comprises sodium bicarbonate in an amount of 50 to 70 wt % based on the second effervescent material. In a preferred aspect the second effervescent material comprises sodium bicarbonate in an amount of 55 to 70 wt % based on the second effervescent material. In a preferred aspect the second effervescent material comprises sodium bicarbonate in an amount of 60 to 70 wt % based on the second effervescent material. In a preferred aspect the second effervescent material comprises sodium bicarbonate in an amount of approximately 62 wt % based on the second effervescent material.

In a preferred aspect the second effervescent material comprises citric acid in an amount of 24 to 40 wt % based on the second effervescent material. In a preferred aspect the second effervescent material comprises citric acid in an amount of 24 to 35 wt % based on the second effervescent material. In a preferred aspect the second effervescent material comprises citric acid in an amount of 26 to 32 wt % based on the second effervescent material. In a preferred aspect the second effervescent material comprises citric acid in an amount of 27 to 31 wt % based on the second effervescent material. In a preferred aspect the second effervescent material comprises citric acid in an amount of approximately 29 wt % based on the second effervescent material.

In a preferred aspect the second effervescent material comprises cream of tartar in an amount of 2 to 6 wt % based on the second effervescent material. In a preferred aspect the second effervescent material comprises cream of tartar in an amount of 2 to 5 wt % based on the second effervescent material. In a preferred aspect the second effervescent material comprises cream of tartar in an amount of 2 to 4 wt % based on the second effervescent material. In a preferred aspect the second effervescent material comprises cream of tartar in an amount of 2.5 to 3.5 wt % based on the second effervescent material. In a preferred aspect the second effervescent material comprises cream of tartar in an amount of approximately 3 wt % based on the second effervescent material.

The second effervescent material of the surfactant product of the present invention comprises cream of tartar. Cream of tartar is also known as potassium bitartrate or potassium hydrogen tartrate. It is the mono-potassium salt of 2,3-dihydroxybutanedioic acid. Thus, the cream of tartar used in the surfactant product of the present invention encompasses any product which is considered to be cream of tartar by virtue of it substantially comprising potassium hydrogen tartrate. In one embodiment, the cream of tartar of the surfactant product is potassium hydrogen tartrate.

In a preferred aspect the second effervescent material further comprises a fragrance. Preferably the fragrance is present in an amount of 0.5 to 4 wt % based on the second effervescent material. In a preferred aspect the second effervescent material comprises fragrance in an amount of 1 to 4 wt % based on the second effervescent material. In a preferred aspect the second effervescent material comprises fragrance in an amount of 2 to 4 wt % based on the second effervescent material. In a preferred aspect the second effervescent material comprises fragrance in an amount of 2.5 to 3.5 wt % based on the second effervescent material. In a preferred aspect the second effervescent material comprises fragrance in an amount of approximately 3 wt % based on the second effervescent material.

In a preferred aspect the second effervescent material comprises
- surfactant in an amount of 0.5 to 5 wt % based on the second effervescent material and sodium bicarbonate in an amount of 40 to 75 wt % based on the second effervescent material.
- In a preferred aspect the second effervescent material comprises surfactant in an amount of 0.5 to 5 wt % based on the second effervescent material and citric acid in an amount of 24 to 40 wt % based on the second effervescent material.
- surfactant in an amount of 0.5 to 5 wt % based on the second effervescent material and cream of tartar in an amount of 2 to 6 wt % based on the second effervescent material.
- sodium bicarbonate in an amount of 40 to 75 wt % based on the second effervescent material and citric acid in an amount of 24 to 40 wt % based on the second effervescent material.

sodium bicarbonate in an amount of 40 to 75 wt % based on the second effervescent material and cream of tartar in an amount of 2 to 6 wt % based on the second effervescent material.

citric acid in an amount of 24 to 40 wt % based on the second effervescent material and cream of tartar in an amount of 2 to 6 wt % based on the second effervescent material.

surfactant in an amount of 0.5 to 5 wt % based on the second effervescent material, sodium bicarbonate in an amount of 40 to 75 wt % based on the second effervescent material, and citric acid in an amount of 24 to 40 wt % based on the second effervescent material.

surfactant in an amount of 0.5 to 5 wt % based on the second effervescent material, sodium bicarbonate in an amount of 40 to 75 wt % based on the second effervescent material, and cream of tartar in an amount of 2 to 6 wt % based on the second effervescent material.

surfactant in an amount of 0.5 to 5 wt % based on the second effervescent material, citric acid in an amount of 24 to 40 wt % based on the second effervescent material, and cream of tartar in an amount of 2 to 6 wt % based on the second effervescent material.

sodium bicarbonate in an amount of 40 to 75 wt % based on the second effervescent material, citric acid in an amount of 24 to 40 wt % based on the second effervescent material, and cream of tartar in an amount of 2 to 6 wt % based on the second effervescent material.

surfactant in an amount of 0.5 to 5 wt % based on the second effervescent material, sodium bicarbonate in an amount of 40 to 75 wt % based on the second effervescent material, citric acid in an amount of 24 to 40 wt % based on the second effervescent material, and cream of tartar in an amount of 2 to 6 wt % based on the second effervescent material.

Further Effervescent Materials

The present invention is not limited to only two distinct effervescent materials. A further, third material may be incorporated into the product to provide further effects, for example with regard to effervescence, colour or foam production.

Surfactant Product

The first effervescent material and the second effervescent material are combined to prepare a surfactant product in accordance with the present invention. The surfactant product may of course contain components in addition to the first effervescent material and the second effervescent material. However, in one aspect the surfactant product consists of the first effervescent material and the second effervescent material.

The first effervescent material and the second effervescent material may be combined in any suitable ratio to provide the desired surfactant product. Preferred ratios (based on weight) of first effervescent material to second effervescent material are 90:10 to 10:90, 80:20 to 20:80, 70:30 to 30:70, 60:40 to 40:60, 55:45 to 45:55 and approximately 50:50.

One skilled in the art can readily prepare a product based on these ratios and the amounts of materials based on the first and second effervescent materials. In one preferred aspect the first effervescent material comprises sodium bicarbonate in an amount of 20 to 40 wt % based on the surfactant product. In one preferred aspect the first effervescent material comprises citric acid in an amount of 7.5 to 25 wt % based on the surfactant product. In one preferred aspect the second effervescent material comprises surfactant in an amount of 0.5 to 1.5 wt % based on the surfactant product. In one preferred aspect the second effervescent material comprises sodium bicarbonate in an amount of 18 to 36 wt % based on the surfactant product. In one preferred aspect the second effervescent material comprises citric acid in an amount of 6 to 23 wt % based on the surfactant product. In one preferred aspect the second effervescent material comprises cream of tartar in an amount of 1.25 to 1.75 wt % based on the surfactant product.

In one preferred aspect the first effervescent material comprises sodium bicarbonate in an amount of 20 to 40 wt % based on the surfactant product, the first effervescent material comprises citric acid in an amount of 7.5 to 25 wt % based on the surfactant product, the second effervescent material comprises surfactant in an amount of 0.5 to 1.5 wt % based on the surfactant product, the second effervescent material comprises sodium bicarbonate in an amount of 18 to 36 wt % based on the surfactant product, the second effervescent material comprises citric acid in an amount of 6 to 23 wt % based on the surfactant product and the second effervescent material comprises cream of tartar in an amount of 1.25 to 1.75 wt % based on the surfactant product.

The components of the surfactant product may be selected such that the final product has a density of less than 1 $g/cm^3$, and therefore floats in water, or greater than 1 $g/cm^3$, and therefore sinks in water. A product which floats will tend to move across the surface of the water. This will product patterns of foam as described herein. A product that sinks will tend to provide a 'geyser' or 'whirlpool' effect.

Each of the first effervescent material and the second effervescent material may optionally contain colouring independently of each other. When both materials contain colouring the colours may be selected such that a first colour in the outer material is dispersed in the water in use. When the water penetrates to the inner material a second colour may be dispersed. If this second colour is different to the first it will combine with the first to provide a change of colour to the water.

Process

As discussed herein, the invention provides a process for the production of a surfactant product comprising a first effervescent material and a second effervescent material, wherein each effervescent material is capable of effervescence on contact with water, wherein the rate of effervescence of the first effervescent material is greater than the rate of effervescence of the second effervescent material, and wherein the first and second effervescent materials are distinct from each other and at least one of the effervescent materials envelops the other of the effervescent materials, the process comprising the steps of:

i) preparing the first or second effervescent material;
ii) enveloping the first or second effervescent material with the other of the first or second effervescent material.

In the present process preferably the process comprises the steps of:

i) preparing the first effervescent material;
ii) enveloping the first effervescent material with the second effervescent material.

Preferably the effervescent material of step i), for example first effervescent material, is caused to solidify in a predetermined shape. After the solidification the effervescent material of step i) the other effervescent material, for example second effervescent material is placed round the solid so as to envelop it. The effervescent material of step ii) is also typically caused to solidify in a predetermined shape. Possible shapes include spheres, cube, cuboids and cones.

The shape of the surfactant products of the present invention is not limited. It may be that the surfactant products are provided with a shape which would be aesthetically pleasing and/or which aids in the use of the product. For example, it may be that the surfactant product is produced in such a manner so that it solidifies in a shape which is ergonomically acceptable to the user. Therefore, in one embodiment of the process of the present invention, the mixture of step i) and/or step ii) is pressed into a mould, allowed to solidify, and then turned out to produce the surfactant product.

As described herein, the surfactant product may further comprise one or more cosmetically acceptable additives. In one embodiment, the process further comprises the step of combining with the mixture of step i) and/or step ii) one or more cosmetically acceptable additives as defined above.

It is envisaged that the effervescent material which is enveloped need not be provided as a single discrete material. The effervescent material which is enveloped may be present as 'pockets' of material which are surrounded by the other effervescent material, one material may be dispersed in a single mass of the other material. An analogy can be drawn with an emulsion. Thus, in one example, the first effervescent material may be provided as a number of spheres of material. These spheres of first effervescent material are enveloped by a single mass of the second effervescent material.

Preferred Compositions & Additional Components

The surfactant product of the present invention may also comprise one or more cosmetically acceptable additives. The person skilled in the art is aware of a range of cosmetically acceptable additives which are suitable for incorporation into such compositions. Fruit and herb extracts and juices, vegetable oils and essential oils are all compatible with the composition. Colours, both naturally derived and synthetic can be used to colour the surfactant product. Sodium carbonate may also incorporated into the composition.

In one embodiment, the cosmetically acceptable additives are selected from the group consisting of essential oils, vitamins, fragrances, colourings, clays, vegetable butters, decorative articles and mixtures thereof.

In one embodiment, the cosmetically acceptable additives are present in amount of from about 0.2% to about 3% by weight of the total composition.

The essential oils will be selected based on the fragrance desired, skin type to be treated and other effects desired based on the well known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the surfactant product are selected from Tarragon, Lemon myrtle, Jasmin, Ylang ylang, Labdunum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, Litsea Cubeba, Cardamon, Tonka, and Chamomile blue. In one embodiment, the one or more essential oils present in the surfactant product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the surfactant product of a material, such as a natural material, that has a high vitamin content.

The ingredients in the present invention do not require cosmetic preservatives. The use of cosmetic preservatives can increase the potential to irritate the skin.

The decorative items which may be present in the surfactant product include items such as glitter, paper such as rice paper, sequins, dried or fresh flowers, herbs, vegetables, parts thereof or mixtures thereof. Other enhancing materials such as popping candy may also be incorporated The above ranges provide preferred amounts of each of the components. Each of these ranges may be taken alone or combined with one or more other component ranges to provide a preferred aspect of the invention.

Method

In one aspect of the present invention, there is provided a method comprising contacting the skin of a user with water in which the surfactant product as defined herein has dissolved or in which the surfactant product as defined herein is dissolving. In a typical method water in run in to the bath at acceptable temperature. The user immerses their body in the water and the surfactant product is dropped in to the water. The user then watches the effect of the product on the surface of the water or as it effervesces beneath the surface. The user then bathes in the water.

Examples

The invention will now be described with reference to the following non-limiting example.

A surfactant product having the following composition was prepared.

The formula is as follows:

|  | % By Weight |
|---|---|
| First Effervescent Material |  |
| Sodium Bicarbonate | 31 |
| Fragrance | 1.5 |
| Citric Acid | 15 |
| Second Effervescent Material |  |
| Sodium Bicarbonate | 33 |
| Cream Of Tartar | 1.5 |
| Sodium Laureth Sulfate (Surfactant) | 1.5 |
| Fragrance | 1.5 |
| Citric Acid | 15 |
| TOTAL | 100 |

Method
1. The First Effervescent Material was prepared as follows— Fragrance was dispersed through the Sodium Bicarbonate powder. Citric Acid powder was blended though and the mixture is pressed in to a 'mould' shape.
2. The Second Effervescent Material was prepared as follows—Fragrance was dispersed in to the Sodium Bicarbonate powder. Cream of Tartar was dispersed through this. Surfactant was blended through and finally Citric Acid powder was added and dispersed.
3. The First Effervescent Material was removed from the mould and the Second Effervescent Material as prepared was pressed around it in to a second final mould shape.
4. When the mixture had hardened it was removed from the mould.

The blends can be reversed with First Effervescent Material being pressed around the Second Effervescent Material if required.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A surfactant product comprising a first effervescent composition and a second effervescent composition,
    wherein each effervescent composition is capable of effervescence on contact with water, wherein a rate of effervescence of the first effervescent composition is greater than a rate of effervescence of the second effervescent composition, wherein the first effervescent composition comprises at least sodium bicarbonate and citric acid, wherein the second effervescent composition comprises at least a surfactant, sodium bicarbonate, citric acid and cream of tartar, and wherein the first and second effervescent compositions are distinct from each other and of the second effervescent composition entirely envelops the first effervescent compositions.

2. A surfactant product according to claim 1, wherein the first effervescent composition comprises sodium bicarbonate in an amount of 40 to 75 wt % based on the first effervescent composition.

3. A surfactant product according to claim 2, wherein the first effervescent composition comprises citric acid in an amount of 24 to 40 wt % based on the first effervescent composition.

4. A surfactant product according to claim 1, wherein the second effervescent composition comprises a surfactant in an amount of 0.5 to 5 wt % based on the second effervescent composition.

5. A surfactant product according to claim 1, wherein the second effervescent composition comprises sodium bicarbonate in an amount of 40 to 75 wt % based on the second effervescent composition.

6. A surfactant product according to claim 1, wherein the second effervescent composition comprises citric acid in an amount of 24 to 40 wt % based on the second effervescent composition.

7. A surfactant product according to claim 1, wherein the second effervescent composition comprises cream of tartar in an amount of 2 to 6 wt % based on the second effervescent composition.

8. A surfactant product according to claim 1, wherein the surfactant product has a density of less than 1 $g/cm^3$.

9. A surfactant product according to claim 1, wherein the first effervescent composition is present in an amount of 10 to 90 wt % based on the surfactant product.

10. A surfactant product according to claim 1, wherein the second effervescent composition is present in an amount of 10 to 90 wt % based on the surfactant product.

11. A process for the production of a surfactant product as defined in claim 1 comprising the steps of:
    i) preparing the first effervescent composition;
    ii) enveloping the first effervescent composition with the second effervescent composition.

12. A process according to claim 1, wherein the effervescent composition of step i) is caused to solidify in a predetermined shape.

13. A process according to claim 11, wherein the effervescent composition of step ii) is caused to solidify in a predetermined shape.

14. A product obtained or obtainable by the process of claim 11.

* * * * *